United States Patent
Verhulst et al.

(10) Patent No.: US 12,146,873 B2
(45) Date of Patent: Nov. 19, 2024

(54) METHOD OF OPERATING A PORE FIELD-EFFECT TRANSISTOR SENSOR FOR DETECTING PARTICLES

(71) Applicant: IMEC VZW, Leuven (BE)

(72) Inventors: Anne Verhulst, Houtvenne (BE); Pol Van Dorpe, Spalbeek (BE)

(73) Assignee: IMEC VZW, Leuven (BE)

(*) Notice: Subject to any disclaimer, the term of this patent is extended or adjusted under 35 U.S.C. 154(b) by 185 days.

(21) Appl. No.: 17/849,905

(22) Filed: Jun. 27, 2022

(65) Prior Publication Data

US 2023/0003710 A1 Jan. 5, 2023

(30) Foreign Application Priority Data

Jun. 30, 2021 (EP) .................................. 21182695

(51) Int. Cl.
*G01N 15/06* (2024.01)
*G01N 15/01* (2024.01)
*G01N 33/487* (2006.01)

(52) U.S. Cl.
CPC ... *G01N 33/48721* (2013.01); *G01N 15/0656* (2013.01); *G01N 15/01* (2024.01)

(58) Field of Classification Search
CPC ......... G01N 33/48721; G01N 15/0656; G01N 15/01; G01N 27/4146; G01N 27/4145
See application file for complete search history.

(56) References Cited

U.S. PATENT DOCUMENTS 8,232,582 B2   7/2012  Sauer et al.
8,828,138 B2   9/2014  Bedell et al.
(Continued)

FOREIGN PATENT DOCUMENTS

JP   2014190891 A  * 10/2014  ............. G01N 27/30
WO   WO-2013016486 A1   1/2013
WO   WO-2019120642 A1   6/2019

OTHER PUBLICATIONS

Dongyan Xu et al. "Ultra-Sensitive Fluidic Sensors by Integrating Fluidic Circuits and MOSFETS", Proceedings of IMECE2007, 2007 ASME International Mechanical Engineering Congress and Exposition, IMECE 2007-42518, 2007, pp. 1-6.
(Continued)

*Primary Examiner* — Akm Zakaria
(74) *Attorney, Agent, or Firm* — MOSER TABOADA

(57) ABSTRACT

A method of operating a pore field-effect transistor (FET) sensor for detecting particles, wherein the pore FET sensor comprises a FET wherein a gate is controlled by a pore filled by a fluid, comprises: controlling a first voltage ($V_{cis}$) to set the FET in a subthreshold region; controlling a second voltage ($V_{trans}$) to set a voltage difference between the first and second voltages ($V_{trans}$) such that an effective difference in gate voltage experienced between a minimum and a maximum effective gate voltage during movement of a particle in the fluid is at least kT/q; and detecting a drain-source current in the FET, wherein the particle passing through the pore modulates the drain-source current for detecting presence of the particle.

14 Claims, 6 Drawing Sheets

(56) References Cited

U.S. PATENT DOCUMENTS

| | | | |
|---|---|---|---|
| 2010/0066348 A1* | 3/2010 | Merz | C12Q 1/6869 |
| | | | 257/253 |
| 2019/0226463 A1 | 7/2019 | Feng et al. | |
| 2021/0310987 A1* | 10/2021 | Xie | C12Q 1/6869 |
| 2022/0221422 A1* | 7/2022 | Shuhendler | G01N 27/4148 |

OTHER PUBLICATIONS

Manoj Sridhar et al. "Experimental characterization of a metal-oxide semiconductor field effect transistor-based Coulter counter", Journal of Applied Physics vol. 103, 104701, 2008, pp. 104701-1-104701-10.

Ping Xie et al. "Local electrical potential detection of DNA by nanowire-nanopore sensors", Nature Nanotechnology Letters, vol. 7, 2011, pp. 119-125.

William M. Parkin et al. "Signal and Noise in FET-Nanopore Devices", ACS Sensors 2018, 3, 313-319.

Ruic et al. "Design and Modeling of a Nanopore Transistor", Single-Molecule Sensors and nanoSystems International Conference (S3IC), 2020, pp. 1-4.

Extended European Search Report in European Patent Application No. 21182695.3 dated Dec. 2, 2021.

\* cited by examiner

METHOD OF OPERATING A PORE FIELD-EFFECT TRANSISTOR SENSOR FOR DETECTING PARTICLES

CROSS REFERENCE TO RELATED APPLICATION

This application claims priority to European Patent Application No. 21182695.3, filed on Jun. 30, 2021, incorporated herein by reference in its entirety.

TECHNICAL FIELD

The present inventive concept relates to a method of operating a pore field-effect transistor sensor for detecting particles. In particular, the present inventive concept relates to detecting particles with a high sensitivity in a pore field-effect transistor.

BACKGROUND

Field-effect transistors (FETs) having a pore are known for use in sensing of particles, such as sensing of single molecules. The pore is used for gating the FET such that when a single molecule is passed through the pore, a current modulation of the FET can be achieved. Thus, a pore FET sensor can be formed, wherein translocation of a single molecule through the pore can affect gating of the FET for allowing detection of the single molecule.

In Ruić et al, "Design and Modeling of a Nanopore Transistor", Single-Molecule Sensors and nanoSystems International Conference (S3IC), Nov. 9-11, 2020, pages 1-4, a nanopore FET is disclosed, wherein the nanopore FET is a transistor wrapped around a nanopore connecting two electrolyte reservoirs. The nanopore FET can detect analyte molecules passing through the nanopore as a change in a source-drain current of the nanopore FET. Designing dimensions of the nanopore FET involves optimizing geometry for formation of a carrier channel in semiconductor around the pore while avoiding leakage current from source to drain. Optimal sensitivity can be expected when potential perturbations by molecules in the nanopore impact electron density in the channel maximally. Sensitivity of the nanopore FET can be defined as maximal change in current due to presence of the molecule normalized by magnitude of the current. Ruić et al discloses that signals (of molecules) can exceed 20%.

Thus, although Ruić et al discusses optimization of sensitivity of the nanopore FET sensor, there is still a need to improve sensitivity in comparison to signals exceeding 20% as reported by Ruić et al.

SUMMARY

An objective of the present inventive concept is to provide a method for operating a pore field-effect transistor to provide a high sensitivity to movement of particles through the pore.

This and other objectives are at least partly met by the invention as defined in the independent claims. Preferred embodiments are set out in the dependent claims.

According to an aspect of the present inventive concept, there is provided method of operating a pore field-effect transistor sensor for detecting particles, wherein the pore field-effect transistor sensor comprises a field-effect transistor having a source, a drain, a dielectric, a gate, and a channel region between the source and the drain, wherein the gate is controlled by a pore filled by an electrically conducting fluid and the pore is configured to extend from a first side to a second side to provide gating of the field-effect transistor from within the pore, and wherein the pore field-effect transistor sensor further comprises a first electrode for setting a first voltage at the first side of the pore and a second electrode for setting a second voltage at the second side of the pore, wherein said method comprises: controlling the first voltage to set the field-effect transistor in a subthreshold region; controlling the second voltage to set a voltage difference between the first voltage and the second voltage such that an effective difference in gate voltage of the field-effect transistor experienced between a minimum effective gate voltage and a maximum effective gate voltage during movement of a particle to be detected in the fluid, wherein the movement of the particle to be detected includes the particle to be detected being outside the pore and being passed through the pore, is at least $kT/q$, where k is Boltzmann's constant, T is temperature of the field-effect transistor, and q is the electron charge; and detecting a drain-source current in the field-effect transistor, wherein the particle to be detected passing through the fluid in the pore is configured to modulate the drain-source current for detecting presence of the particle.

It is an insight of the present inventive concept that sensitivity of a pore field-effect transistor (FET) sensor for detecting particles may be significantly increased by a particular mode of operation of the pore FET sensor. In particular, a signal provided when a particle is present in the pore may be at a completely different level of magnitude compared to a signal when no particle is present in the pore, such that the sensitivity of the sensor is high and that particles may be accurately detected using the pore FET sensor.

According to the present inventive concept, the FET is set into a subthreshold region. This implies that, if the FET is an n-channel FET, a gate-to-source voltage of the FET is below a threshold voltage. Similarly, if the FET is a p-channel FET, a source-to-gate voltage of the FET is below a threshold voltage. Discussion below will mainly be done in relation to an n-channel FET to discuss the gate-to-source voltage being below the threshold voltage, but it should be realized that the FET may alternatively be a p-channel FET and that, in such case, a source-to-gate voltage of the FET is instead below a threshold voltage. The threshold voltage may be defined as a voltage level at which the channel of the FET is turned on so as to allow a current to be easily conducted between drain and source. However, even in the subthreshold region, a current between drain and source will occur. In the subthreshold region, the current varies exponentially with the gate voltage.

It is an insight of the present inventive concept that, when operating the FET in the subthreshold region, a difference in voltages applied to electrodes on opposite sides of the pore can be set such that an effective difference in gate voltage during movement of a particle to be detected in the fluid allows sensing the particle with a very high sensitivity.

When the effective difference in gate voltage between a maximum effective gate voltage and a minimum effective gate voltage is at least $kT/q$, impact of a particle in the pore will be boosted. This is because an exponent factor of the drain-source current will be larger than 1, since the drain-source current is dependent on $e^{V_g/V_t}$ where $V_g$ is the gate voltage and $V_t$ is a thermal voltage that equals $kT/q$. Thus, the minimum effective difference in gate voltage of at least $kT/q$ ensures that an exponential boosting in drain-source current between the maximum and minimum effective gate voltage is provided. This implies that a strong signal can be provided by the particle to be detected passing the pore such that the particle can be detected with a high sensitivity ensuring that the particle is accurately detected over noise in the sensor.

Thanks to the present inventive concept, the pore FET sensor may be operated to ensure a high sensitivity for detecting particles. The pore FET sensor may further be improved by design of characteristics of the pore FET sensor. However, since the sensitivity of the pore FET sensor is high, there may not be a need to e.g. optimizing geometry for formation of a carrier channel in semiconductor in order to ensure that the signal from the particle to be detected is sufficiently strong to allow accurate detection over noise.

As used herein, the term "pore field-effect transistor" should be construed as a FET, wherein a pore is used for providing a gate voltage to the FET. The pore could be separately arranged from the channel region of the FET. For instance, the pore could be provided with an electrode which is directly connected to a gate electrode of the FET arranged close to the channel region, such that a voltage of the gate electrode could be controlled by the electrode of the pore. However, according to an alternative, the pore may be arranged in relation to the channel region, such that the pore may control the gate voltage directly, whereby the gate material is represented by the fluid inside the pore. For instance, the pore may be configured to extend through the channel region.

The pore is configured to allow the particle to be detected to pass through the pore. Further, the pore is configured to have a cross-sectional dimension at least in one location of the pore, such that the particle to be detected blocks the pore to such an extent that potential perturbations within the pore are generated and the effective gate voltage of the FET is changed. Thus, when the particle to be detected passes through the pore, the effective gate voltage of the FET will be changed such that the drain-source current of the FET will be modulated. This enables detecting the particle being passed through the pore.

A cross-sectional dimension of the pore may be related to a size of a type of particle to be detected. Hence, the pore may be dimensioned to be adapted for detecting a particular type of particle, such as a DNA molecule or one strand of a DNA molecule or a protein. The method may thus use a pore FET sensor properly dimensioned in relation to the particle to be detected. Typically, the type of particle to be detected is known, being a particle of interest, such that the pore FET sensor may be properly dimensioned.

The cross-sectional dimension of the pore may be small such that small particles to be detected will block a substantial part of the cross-section of the pore. For instance, the pore may be a nanopore, such as having a circular cross-section with a diameter less than 100 nm, but it should be realized that the pore may in other embodiments be larger, if larger molecules or particles are to be detected.

The pore is filled by a fluid during operation such that the particle to be detected may be transported through the fluid for passing through the pore. A sample to be analyzed may be inserted into the fluid which is previously provided in the pore FET sensor. Alternatively, the sample may be introduced with the fluid into the pore FET sensor. The fluid (and the sample) may further be removed from the pore FET sensor and replaced so as to allow the pore FET sensor to analyze further samples.

Each sample may comprise a plurality of particles to be detected. The pore may be sized in relation to the particles to be detected such that two particles cannot pass in parallel through the pore, but rather pass in sequence through the pore. Additionally or alternatively, the pore FET sensor may comprise a control element at an entry into the pore, which control element ensures that a single particle to be detected is entered at a time into the pore.

The FET is beneficially a metal-oxide-semiconductor field-effect transistor (MOSFET) to provide current through the transistor in the subthreshold region.

For an n-channel FET, the second voltage is more negative than the first voltage. The first voltage is controlled to set the FET in the subthreshold region. Then, the second voltage should be more negative than the first voltage such that the second voltage also ensures that the FET is in the subthreshold region. For a p-channel FET, the second voltage is more positive than the first voltage to ensure that the FET is in the subthreshold region.

The minimum effective gate voltage may be defined by the second voltage, when the particle to be detected is at the first side of the pore. In this case, the particle to be detected blocks the pore at the first side, such that the second voltage may control the voltage through the pore. However, it should be realized that the minimum effective gate voltage need not in this case be exactly equal to the second voltage, because e.g. entrance of the pore represents a resistance. This implies that there may be a drop in electrical potential through the pore. Similarly, the maximum effective gate voltage may be defined by the first voltage, when the particle to be detected is at the second side of the pore.

However, it should be realized that the minimum and maximum effective gate voltage may instead be defined when no particle is present in the pore and when the particle to be detected is configured to substantially block a cross-section of the pore. This may for instance occur when the pore has a non-uniform cross-section such that the particle to be detected will only substantially affect the gate voltage when the particle to be detected is arranged at an end of the pore having a smallest cross-section.

The effective difference in gate voltage need not correspond to the difference between the first voltage and the second voltage, since, as mentioned above, there may be a drop in electrical potential through the pore such that the maximum and minimum effective gate voltages are not necessarily directly defined by the first voltage and the second voltage, respectively.

The source and drain may be biased by constant voltages. The source may be connected to ground voltage. It should be realized that gate-to-source voltage is configured to control the FET and that "gate voltage" and "gate-to-source voltage" are used interchangeably herein.

According to an embodiment, the voltage difference between the first voltage and the second voltage additionally drives the particle to be detected through the pore.

It should be realized that the voltage difference between the first voltage and the second voltage may drive the particles to be detected through the pore. If the particles are positively charged, the particles to be detected may be driven from the first side to the second side of the pore towards the lower potential set by the second voltage. If the particles are negatively charged, the particles to be detected may be driven from the second side to the first side.

Also, the electrically conducting fluid may be provided with salt ions (or other ions) such that presence of an electric field in the fluid due to the difference between the first voltage and the second voltage may create a force on the fluid to generate a movement in the fluid that may drag along uncharged parts of the fluid, such as uncharged particles to be detected.

This implies that the voltage difference provided for enabling detecting the particle to be detected with a high sensitivity may also control flow of the particle to be detected through the pore.

However, it should be realized that alternatively or additionally, the driving of particles to be detected through the pore may be provided by in other manners. This may be particularly useful for driving uncharged particles to be detected.

For instance, driving of particles may be provided by a pressure difference between the first side and the second side of the pore and/or by a difference in concentration of the particles to be detected or of ions in the fluid, resulting in a fluid flow through the pore dragging particles to be detected along the fluid flow.

It should be realized that detection of the particle to be detected may be facilitated by prior knowledge of a sign of a charge (if any) of the particle to be detected. However, this may typically be known.

It should be realized that the current between drain and source may flow either from drain to source (for an n-channel FET) or from source to drain (for a p-channel FET) or even from source to drain in an n-channel FET if allowed by surrounding circuit, since the FET may typically have a symmetric design. The term "drain-source current" should therefore be construed as a current between drain and source which may either flow from drain to source or from source to drain.

According to an embodiment, the pore is configured to extend through the channel region between the source and the drain.

The pore may thus be configured to extend in a direction transverse to a direction between the source and the drain. The pore may extend in an orthogonal angle to the direction between the source and the drain. However, it should be realized that the angle may differ from orthogonal, as long as the pore extends through the entire channel region from the first side to the second side.

This implies that detecting of particles may be provided in a compact pore FET sensor with the pore arranged within the channel region.

According to an embodiment, the method further comprises identifying the particle to be detected passing through the fluid in the pore by identifying a change in the drain-source current.

Thanks to the particle to be detected providing a modulation of the drain-source current, detection of the particle to be detected may be provided by identifying a change in the drain-source current.

The identifying of the change may involve identifying a difference of the drain-source current when the particle to be detected is present in the pore comparted to the drain-source current when no particle to be detected is present in the pore.

The identifying of the change may involve identifying a difference of the drain-source current when the particle to be detected is arranged at the first side of the pore compared to the drain-source current when the particle to be detected is arranged at the second side of the pore.

According to an embodiment, the first and second voltages are controlled to set the effective difference in gate voltage such that a difference between a maximum detected drain-source current compared to a minimum detected drain-source current is larger than 100%, such as larger than 200%, of the minimum detected drain-source current.

Thanks to the effective difference in gate voltage provided by the present inventive concept, an exponential boosting in drain-source current difference between the maximum and minimum effective gate voltage is provided. This implies that the difference between the maximum and minimum detected drain-source current may be at least 200%.

Thanks to a large difference between the maximum and minimum detected drain-source current, the particle to be detected can be detected with a high sensitivity allowing accurate detection of the particle to be detected.

According to an embodiment, the particle to be detected has a size in relation to the pore so as to modify electrical potential distribution in the pore such that location of the particle to be detected functions as a controller to set resistive values in the fluid inside the pore such that the location of the particle determines the resistive divider values and the effective gate voltage.

Hence, the pore and the particle to be detected are sized such that the particle to be detected blocks the pore to such an extent that the electrical potential distribution in the pore is substantially changed. This implies that the location of the particle to be detected along the pore between the first side and the second side controls resistive divider values such that the effective gate voltage is highly dependent on the location of the particle to be detected in the pore.

According to an embodiment, the second voltage defines a minimum effective gate voltage of the field-effect transistor when the particle to be detected is passed through the fluid in the pore.

This may be combined with the first voltage defining the maximum effective gate voltage when the particle to be detected is passed through the fluid in the pore.

Hence, both the maximum effective gate voltage and the minimum effective gate voltage may be provided when the particle to be detected is passed through the fluid in the pore. The maximum effective gate voltage may be larger than an effective gate voltage when no particle is in the pore and the minimum effective gate voltage may be smaller than an effective gate voltage when no particle is in the pore. This implies that a larger effective difference in gate voltage may be provided compared to if the minimum effective gate voltage is defined when no particle is in the pore.

According to an embodiment, an electrolyte fluid is provided at the first side and the second side, and the controlling of the first voltage is provided by applying the first voltage to a first electrode in contact with the electrolyte fluid at the first side and the controlling of the second voltage is provided by applying the second voltage to a second electrode in contact with the electrolyte fluid at the second side.

Hence, the electrolyte fluid provides an electrical potential distribution between the first side and the second side of the pore.

According to an embodiment, an area of a minimum cross-section of the pore is set in relation to the particle to be detected such that an area of a maximum cross-section of the particle to be detected is larger than 50% of the area of the minimum cross-section of the pore, if the particle to be detected is uncharged, and the area of the maximum cross-section of the particle to be detected is larger than 10% of the area of the minimum cross-section of the pore, if the particle to be detected is charged.

Thanks to the particle to be detected having appropriate size in relation to the cross-section of the pore, it may be ensured that the location of the particle to be detected functions as controller for setting the resistive divider values in the fluid inside the pore.

A charged particle affects the electrical potential distribution to a higher extent than an uncharged particle, such that the charged particle could be smaller compared to the cross-section of the pore than an uncharged particle.

According to an embodiment, the pore has a uniform cross-section along the extension from the first side to the second side.

This implies that the particle to be detected may affect electrical potential distribution in the pore along translocation of the particle to be detected between the first side and the second side. In this case, minimum and maximum effective gate voltage may be defined when the particle is arranged at the first side and the second side, respectively.

It should be realized that the pore need not necessarily have a uniform cross-section. According to an alternative, the pore may have a shape of a truncated cone, such that the pore provides a minimum cross-section at one end of the pore and a maximum cross-section at an opposite end of the pore.

According to an embodiment, a length of the pore along the extension from the first side to the second side is longer than a length of the particle to be detected affecting the gate voltage.

Thanks to the pore being longer than the particle to be detected, the particle to be detected may not be arranged simultaneously at the first side and at the second side of the pore such that a substantial effective difference in gate voltage during movement of a particle to be detected in the fluid may be detected. This ensures accurate detection of the particle to be detected.

It should be realized that a length affecting the gate voltage need not correspond to an absolute length of the particle to be detected. For instance, the particle to be detected may comprise a portion having a relatively large cross-section and further comprise e.g. a tail portion with a very narrow cross-section. In such case, only the portion with a large cross-section would affect the gate voltage such that the pore needs to be longer than a length of the portion of the particle with a large cross-section.

A portion of the particle to be detected being relevant for affecting the gate voltage may be defined as a portion of the particle having a cross-section larger than 50% of the area of the minimum cross-section of the pore, if the particle to be detected is uncharged, or a portion of the particle having a cross-section larger than 10% of the area of the minimum cross-section of the pore, if the particle to be detected is charged.

A portion of the particle to be detected being relevant for affecting the gate voltage may be defined as a portion of the particle where charge is distributed, when the particle to be detected is charged.

According to embodiments, a length of the pore along the extension from the first side to the second side is longer than a length of the particle to be detected. It should be realized that the particle to be detected may be shaped like a sphere or a spheroid. In such case, the length of the pore may be longer than the length of the particle to be detected.

Although the length of the pore being longer than a length of the particle to be detected affecting the gate voltage may facilitate accurate detection of the particle to be detected, it should be realized that detection of particles to be detected may still be achieved, even if the pore is shorter than the particle to be detected.

According to an embodiment, the method further comprises providing surface charges on a surface of the pore along the extension from the first side to the second side, wherein the surface charges are of an opposite sign to a charge of the particle to be detected.

Having surface charges on the surface of the pore implies that the fluid in the pore may exhibit charge carriers of an opposite sign. Hence, when the particle to be detected is moved through the pore, there may be a local depletion of charges of the same sign in the fluid. The local depletion is induced by the particle to be detected being arranged in the pore. This implies that the introduction of the particle to be detected in the pore may change the fluid current flow through the pore to a large extent so as to increase effective difference in the gate voltage when the particle to be detected is moved through the pore.

It should be realized that providing surface charges of a same sign as a charge of the particle to be detected may also allow detection of the particle to be detected. However, detection may be more efficiently made if the surface charges and the charge of the particle to be detected are of opposite signs.

According to an embodiment, a concentration of the surface charges is in a range of $1\text{-}10*10^{13}$ cm$^{-2}$.

Such surface charge concentration may advantageously increase effective difference in the gate voltage when the particle to be detected is moved through the pore.

If the surface charge concentration is very high, the surface charges could cause a high ion concentration in the fluid in the pore, such that an impact of the charge of the particle to be detected on the effective gate voltage may be reduced and, hence, blockage of electrical potential distribution in the pore by the particle to be detected may be reduced. Therefore, the surface charge concentration should preferably not be too high.

According to an embodiment, the method further comprises identifying multiple particles to be detected passing through the fluid in the pore forming a chain through the pore, wherein the length of the chain is shorter than 70% of a length of the pore along the extension from the first side to the second side.

Thanks to the pore being longer than the chain of multiple particles to be detected, there will not be particles arranged simultaneously at the first side and at the second side of the pore such that a substantial effective difference in gate voltage during movement of the multiple particles to be detected in the fluid may be detected. This ensures accurate detection of the multiple particles.

According to an embodiment, the length of the chain is shorter than 50% of a length of the pore along the extension from the first side to the second side. This may further ensure accurate detection of the multiple particles.

According to an embodiment, the particle to be detected comprises multiple labels bonded to sites of a long chain, wherein a length of the pore along the extension from the first side to the second side is shorter than 70% of a distance between adjacent labels among the multiple labels.

By using labels, the particle to be detected may thus be very long, exceeding the length of the pore. Thus, the particle to be detected may modulate the drain-source current of the pore FET via label(s) bonded to the particle to be detected.

The label may comprise a molecule that is bonded to the long chain of the particle to be detected. The label may provide a charge and/or size so as to ensure that the site on the long chain with the label will cause an effective difference in gate voltage when the particle to be detected with the label is moved through the pore. The long chain of the particle to be detected may be sufficiently small such that portions of the long chain to which no label is bonded may not affect or may insignificantly affect the effective gate voltage of the pore FET.

Thanks to the pore being shorter than 70% of a distance between adjacent labels, there will not be labels arranged simultaneously at the first side and at the second side of the pore such that a substantial effective difference in gate voltage during movement of the particles to be detected in the fluid may be detected. This ensures accurate detection of the multiple labels bonded to a common long chain of the particle to be detected.

According to an embodiment, the pore is a solid-state pore formed in a solid-state material.

Using a pore FET with a solid-state pore for detecting particles may ensure that the pore withstands being subject to the voltage difference based on the first voltage and the second voltage.

According to an embodiment, a biological membrane is arranged at the first side of the pore and having a biological pore aligned with the pore for assisting in driving particles to be detected through the pore.

The biological membrane may control a speed of the particle to be detected through the biological pore in the biological membrane. In particular, in combination with an enzyme, a speed of DNA passing through the biological membrane may be reduced compared to if DNA passes through the biological membrane without the enzyme. Hence, the biological membrane may slow down speed of particles to be detected, which also implies that the speed of particles to be detected through the pore may be slowed down. A lower speed of the particle to be detected through the pore allows use of a lower sampling rate of the drain-source current in the FET, which may be used for improving a signal-to-noise ratio for detecting the particle to be detected.

In comparison to a solid-state pore, there is a higher risk that a biological membrane would break when being subject to a large voltage difference across the membrane. Hence, the biological membrane may be advantageously used in combination with a solid-state pore. The biological membrane may be arranged at one side of the pore, such that the biological membrane is subject to a smaller voltage difference than the voltage difference experienced by the pore. The biological membrane may thus be used for controlling speed of the particle to be detected, while the solid-state pore may be used for providing a pore that withstands the voltage difference caused by the first voltage and the second voltage.

According to another embodiment, a biological pore may be attached and aligned with the pore without presence of a biological membrane. Further, the biological pore may be provided with an enzyme to regulate speed of DNA passing through the biological pore.

According to an embodiment, the pore is provided with a thin dielectric layer at the surface of the pore along the extension from the first side to the second side, and wherein a surface of the channel region facing an electrolyte fluid at the first side and the second side, respectively, is provided with a thick dielectric layer.

When the pore is configured to extend through the channel region, electrolyte fluid may be arranged in relation to a surface of the channel region. The pore then extends from a first side corresponding to the surface of the channel region to a second side, which may correspond to an opposite surface of the channel region. The electrolyte fluid being arranged in relation to the surface of the channel region implies that gating of the FET could be provided by potential of the electrolyte fluid in relation to the channel region. However, thanks to use of a thick dielectric layer (thicker than the thin dielectric layer at the surface of the pore), gating action of the electrolyte fluid is limited. This implies that the gating of the FET is dominated by the pore, such that the particle to be detected passing through the pore has a high impact on the gating of the FET.

According to an embodiment, the gating action of the electrolyte fluid on the surface of the channel region is less than 10% of the gating action through the pore.

According to an embodiment, the method further comprises calibrating the pore field-effect transistor sensor for setting a maximum sensitivity, wherein the calibrating comprises: setting the first voltage equal to the second voltage to obtain characteristics of drain-source current in relation to the first voltage; determining an off voltage value of the first voltage corresponding to a lowest measurable current of the drain-source current; determining a saturation voltage value of the first voltage corresponding to a transition from linear to saturation region of the field-effect transistor; biasing the first voltage using the saturation voltage value and biasing the second voltage using the off voltage value; iteratively increasing the first voltage and decreasing the second voltage until the gate voltage when a particle is arranged in the pore at the first side corresponds to the off voltage value and the gate voltage when the particle is arranged in the pore at the second side corresponds to the saturation voltage value; and determining first voltage value and second voltage value to be used in operation of the pore field-effect transistor sensor based on end values of the iterative increasing of the first voltage and decreasing of second voltage.

Thanks to such calibration, the sensitivity of the pore FET sensor may be optimized for the settings of the pore FET sensor (design of the pore FET sensor is fixed, the particle to be detected is known). This implies that the pore FET sensor may be set to be used with optimal values for the first voltage and the second voltage so as to allow detection of the particle to be detected with high accuracy.

According to an embodiment, the pore is a nanopore having a cross-sectional diameter smaller than 10 nm.

Using a nanopore with a circular cross-section having a diameter smaller than 10 nm may be useful e.g. for detecting of DNA strands or proteins. For instance, when detecting DNA strands, a cross-sectional diameter of 5 nm may be advantageously used.

It should be realized that the pore need not necessarily have a circular cross-section. Thus, the pore may alternatively be a nanopore with a cross-section having a dimension smaller than 10 nm. In this regard, dimension of the nanopore may be construed as a largest distance of a straight line within the cross-section, such as a distance between opposite sides in a square-shaped cross-section.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1A:
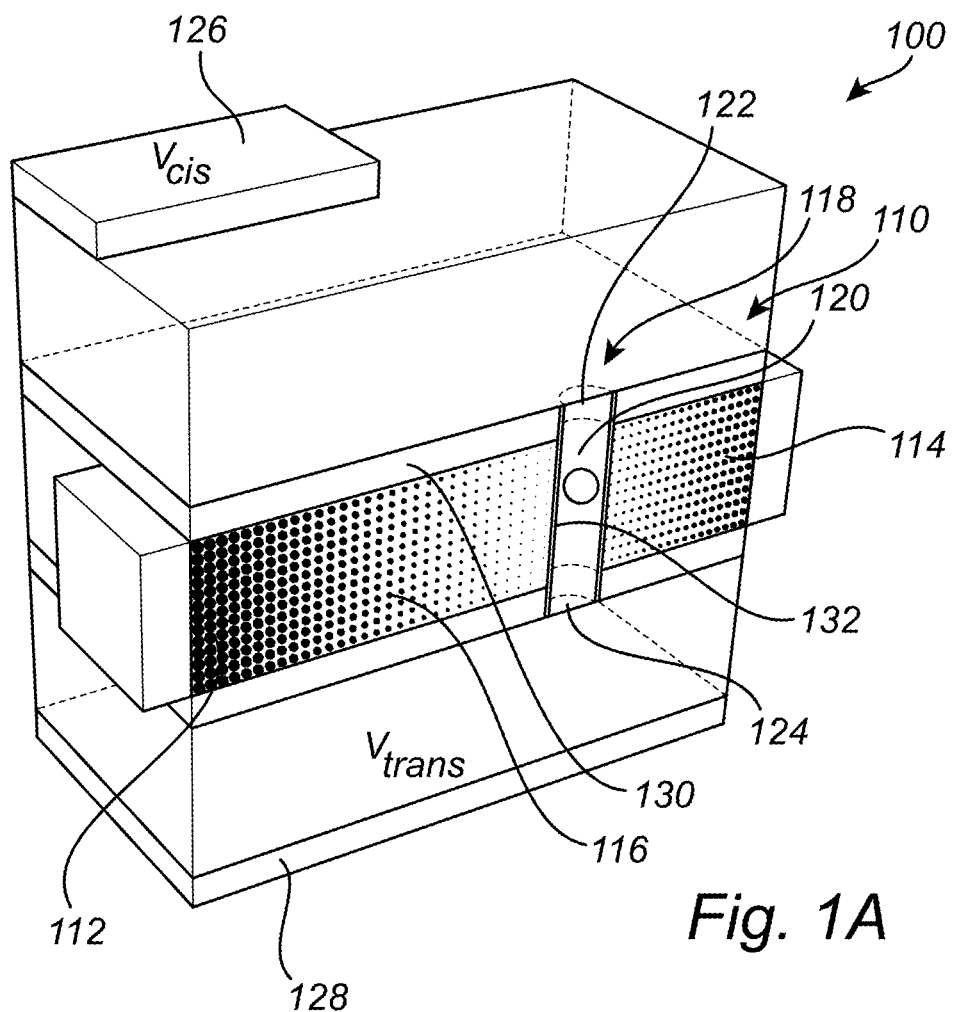
FIG. 1A is a schematic view of a pore field-effect transistor sensor according to an embodiment.

Referring now to FIG. 1A, a sensor 100 using a pore field-effect transistor (FET) 110 will be described.

The pore FET 110 comprises a source 112, a drain 114, a dielectric, and a channel region 116 between the source 112 and the drain 114. The channel region 116 may be controlled by a gate 118 so as to control a drain-source current through the pore FET 110. In the embodiment shown in FIG. 1A, the gate 118 comprises a pore 120.

The pore FET 110 may be formed in a semiconductor material. For instance, the pore FET 110 may be formed as a silicon-on-insulator device. The pore 120 may be formed to extend through semiconductor material so as to form a solid-state pore formed in a solid-state material.

The FET 110 is configured such that an electrical potential in the pore 120 defines a gate voltage for providing gating of the FET from within the pore 120. This implies that, during movement of a particle 140 to be detected though the pore 120, the electrical potential in the pore 120 is affected such that an effective gate voltage is changed, and the drain-source current is modulated. The particle 140 to be detected will affect the effective gate voltage when a charge and a size of the particle 140 is sufficiently large in relation to a cross-sectional dimension of the pore 120.

As shown in FIG. 1A, the pore 120 may extend through the channel region 116 so as to provide gating from a pore 120 extending within the channel region 116.

The pore 120 is configured to have an elongate extension from a first side 122 to a second side 124. Thus, a length of the pore 120 may be substantially larger than the cross-sectional dimension of the pore 120.

The pore 120 may be a nanopore having a cross-sectional diameter smaller than 10 nm. As will be described below, the cross-sectional size of the pore 120 should be adapted to the cross-sectional size of the particle 140 to be detected such that the particle 140 can block a substantial portion of a cross-sectional area of the pore 120. Hence, if small particles are to be detected, the cross-section of the pore 120 should not be too large. Using a nanopore with a circular cross-section having a diameter smaller than 10 nm may be useful e.g. for detecting of DNA strands. When detecting DNA strands, a cross-sectional diameter of 5 nm may be advantageously used.

The pore 120 may provide a fluid connection between a first spacing at the first side 122 and a second spacing at the second side 124. The pore 120 and the first and second spacings may be filled by an electrically conducting fluid, wherein the fluid is configured to define the electrical potential in the pore 120 which is affected by movement of the particle 140 through the pore 120. The first and second spacings may be separated from each other except for the connection through the pore 120. This implies that a difference in electrical potential between the fluid in the first spacing and the fluid in the second spacing causes a difference in electrical potential through the pore 120.

The fluid may be an electrolyte solution, which comprises ions providing an electrical potential of the electrolyte solution. The electrolyte solution may for instance be an aqueous solution in which a soluble salt is provided, which dissociates in cations and anions to form an electrically conducting fluid. Also, hydrogen and hydroxide ions may be added or formed in the aqueous solution.

The electrical potential at the first side 122 of the pore 120 may be controlled by a first electrode 126, which is configured to be in contact with the electrolyte solution in the first spacing, whereas the electrical potential at the second side 124 of the pore may be controlled by a second electrode 128, which is configured to be in contact with the electrolyte solution in the second spacing. Thus, by controlling the voltages applied to the first electrode 126 and the second electrode 128, the electrical potential within the electrolyte solution and in particular through the pore 120 may be controlled.

As shown in FIG. 1A, the pore 120 may extend through the channel region 116 of the FET 110 with the first spacing and second spacing arranged on opposite sides of the channel region 116. The channel region 116 may further be covered by a thick dielectric layer 130, e.g. an oxide, so as to isolate the electrolyte solution in the first and second spacing, respectively, from the channel region 116. Further, a wall surface of the pore 120 may be provided with a thin dielectric layer 132 along the extension of the pore 120 from the first side 122 to the second side 124. This implies that gating of the FET 110 may be provided dominantly from within the pore 120.

The thick dielectric layer 130 may thus be sufficiently thick in relation to the thin dielectric layer 132 so that an impact on the gate voltage is predominantly provided from within the pore 120 and less than 10% of a gating action of the FET 110 is provided through the thick dielectric layer 130.

It should be realized that further layers may be provided on either side of the channel region 116 so as to provide further separation of the electrolyte solution from the channel region 116. For instance, at one side of the pore 120, a substrate may be provided. However, it should be realized that this may imply that the length of the pore 120 may need to be relatively long, as the pore 120 needs to extend through the substrate as well as through the channel region 116.

Also, a dielectric stack may be provided comprising more than one layer of dielectric material. Further, a passivation layer may be provided between a dielectric layer and the fluid. The passivation layer could be used for creating a desired surface charge (as described below).

The thick dielectric layer 130 and the thin dielectric layer 132 may be formed from different materials. The materials may have different iso-electric point (pH value at which surface charge of the material is neutral). This may be used for achieving a change of sign of a surface charge inside the pore 120 compared to at a surface above/below the channel region 116 facing the first and second spacing, respectively.

Figure 1B:
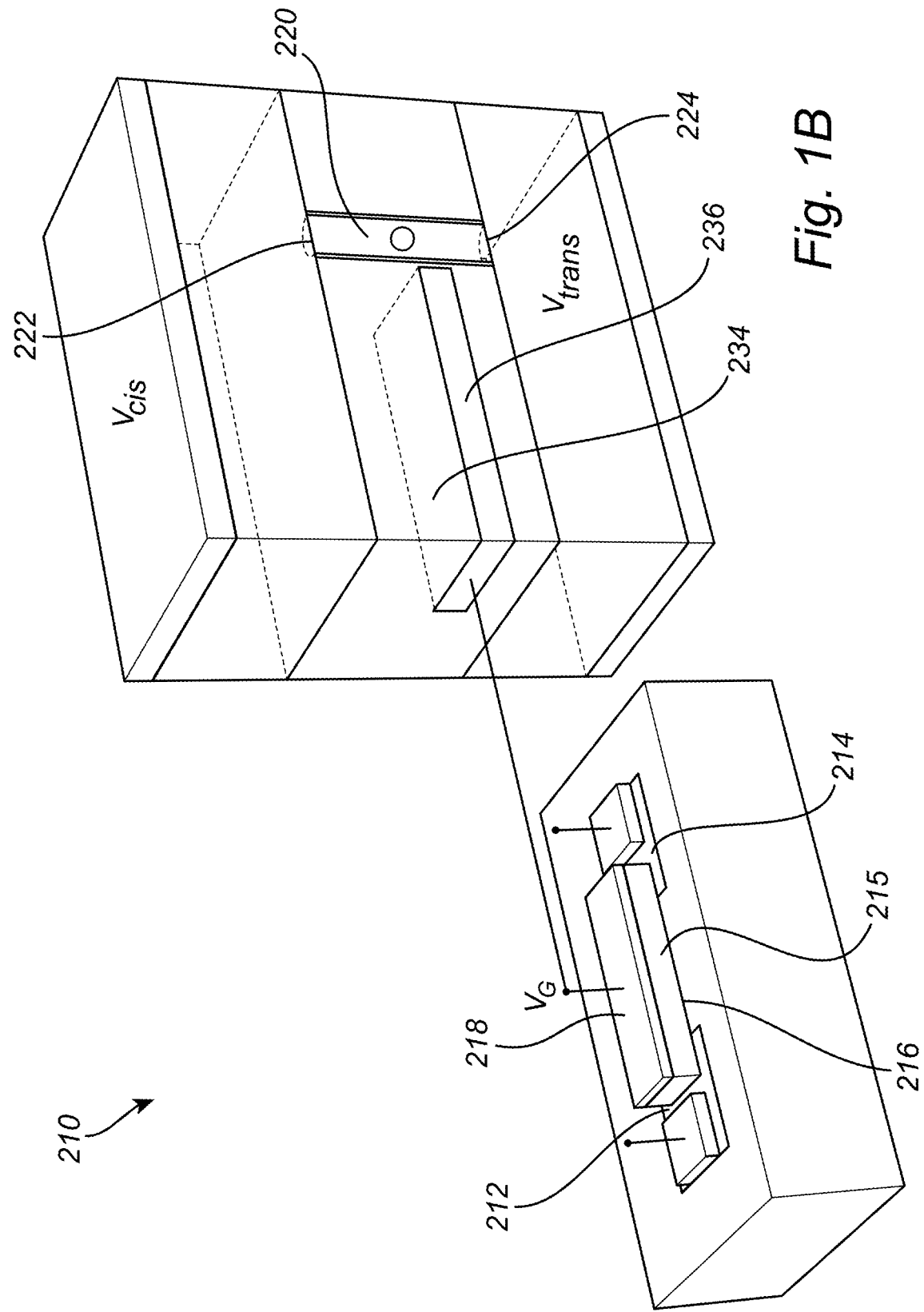
FIG. 1B is a schematic view of a pore field-effect transistor sensor according to another embodiment.

Referring now to FIG. 1B, an alternative arrangement of the pore 220 in relation to the FET 210 will be described. As shown in FIG. 1B, the gate voltage may alternatively be controlled by the pore 220 being physically separate from the channel region 216 of the FET 210. The pore 220 may then be provided to extend through a material layer 234 from a first side 222 to a second side 224, with an electrode 236 formed by a conductive material arranged within the material layer 234. The electrode 236 may be formed by a metal layer providing a highly conducting material. The electrode 236 may be a thin metal layer or a two-dimensional material, such as metallic graphene. The electrode 236 could be formed by a planar layer having a uniform cross-section throughout the layer, but it should be realized that the electrode 236 could alternatively have non-uniform widths or thicknesses. The electrode 236 may surround the pore 220 completely or only be arranged in relation to one side of the pore 220 (as illustrated in FIG. 1B).

The material layer 234 may be formed from a dielectric. The electrode 236 may provide a conductive layer at a particular height in the pore 220. As shown in FIG. 1B, there is a dielectric material at the interface of the fluid in the pore 220 to the electrode 236, but the electrode 236 may alternatively be in direct contact with the fluid. The dielectric material at the interface provides more stable operation of the sensor. The thickness of the dielectric material between the electrode 236 and the fluid in the pore 220 should be as small as possible to provide a good capacitive coupling between the fluid and the electrode 236.

According to an embodiment. the electrode 236 may comprise a combination of more than one highly conductive material, forming a stack of layers of different highly conductive materials. The stack may be arranged to face the fluid in the pore 220 such that a single material forms the interface towards the pore 220. This may be particularly advantageous if the electrode 236 is in direct contact with the fluid in the pore 220, as this may allow to optimize the stack of highly conductive materials for trade-off between high conductivity and good compatibility with the fluid, as one material will form the interface with the fluid and may be selected in view of compatibility with the fluid and other material(s) in the stack may be selected in view of highest conductivity.

The electrode 236 is arranged at a distance from the first side 222 and the second side 224. Preferably, the electrode 236 is arranged at a center of the material layer 234, but the electrode 236 may be arranged closer to the first side 222 or the second side 224.

According to an alternative, a side pore may be arranged to extend in a direction substantially perpendicular to the extension of the pore 220. The electrode 236 may then be arranged in relation to the side pore for providing a gating voltage through the side pore.

In the embodiment of FIG. 1B, the FET 210 is separate to the pore 220. As schematically illustrated in FIG. 1B, the FET 210 comprises a source 212, a drain 214, a dielectric 215, and a channel region 216 between the source 212 and the drain 214. The channel region 216 may be controlled by a gate 218 so as to control a drain-source current through the FET 210. It should be realized that the FET 210 is schematically illustrated in FIG. 1B and that other designs of the FET 210 are conceivable as would be understood by the person skilled in the art. For instance, a FinFET, a gate-all-around FET, a nanosheet or forksheet FET could be used.

The electrode 236 is connected to the gate 218 for providing a gate voltage of the gate 218 of the FET 210. Thus, the voltage provided by the electrode 236 being arranged in relation to the pore 220 may be controlled in a corresponding manner as described for the FET 110.

The electrode 236 is preferably connected to the gate 218 through a highly conductive material with as short length as possible (in view of manufacturing design of the sensor) such that capacitive coupling of connecting material to surroundings is small. The voltage of the gate 218 can thus be controlled by the electrode 236 of the pore 220.

Figure 2:
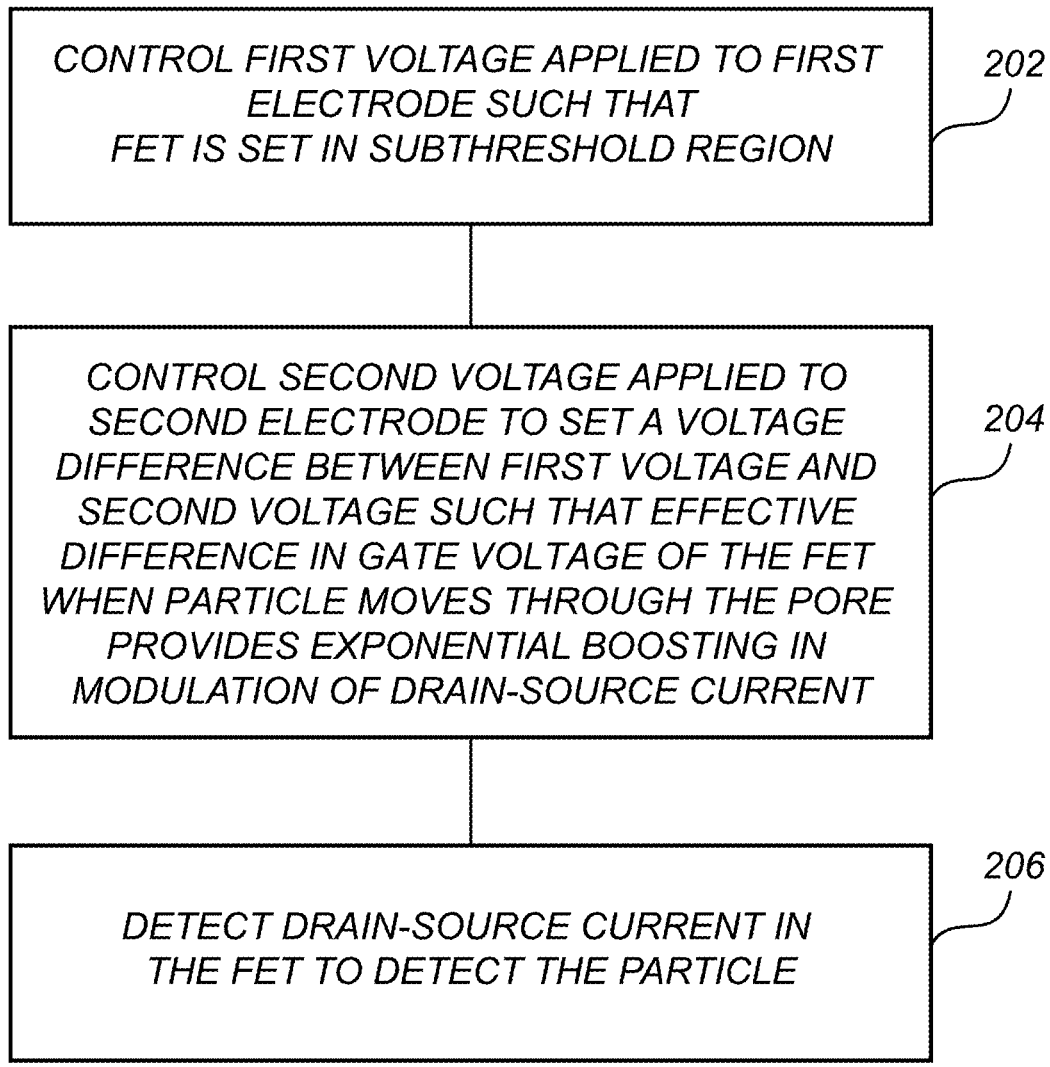
FIG. 2 is a flowchart of a method for operating a pore field-effect transistor sensor for detecting particles moving through the pore.

Referring now to FIG. 2, a method of operating the pore FET sensor 100 for detecting the particle 140 will be described.

The method may comprise providing a sample into the pore FET sensor 100. The sample may comprise particles 140 to be detected in the pore FET sensor 100. The sample may be provided in an electrolyte solution that is inserted into the pore FET sensor 100 to fill the first spacing, the second spacing and the pore 120. Alternatively, the electrolyte solution may be provided initially into the pore FET sensor 100 and the sample may be introduced into the electrolyte solution in the pore FET sensor 100. It should further be realized that the electrolyte solution with a sample may be replaced in the pore FET sensor 100 to allow multiple samples to be analyzed using the pore FET sensor 100.

The method comprises controlling 202 the first voltage $V_{cis}$ applied to the first electrode 126 such that the FET 110 is set in a subthreshold region. This implies that the drain-source current will vary exponentially with the gate voltage of the FET 110.

The method further comprises controlling 204 the second voltage $V_{trans}$ applied to the second electrode 128 to set a voltage difference $V_{cis/trans}=V_{cis}-V_{trans}$ between the first voltage $V_{cis}$ and the second voltage $V_{trans}$. The voltage difference $V_{cis/trans}$ is set such that an effective difference in gate voltage of the FET 110 obtained by movement of the particle 140 through the pore 120 is sufficiently high to provide exponential boosting in modulation of drain-source current.

The method further comprises detecting 206 the drain-source current in the FET 110, wherein the particle 140 to be detected passing through the fluid in the pore 120 is configured to modulate the drain-source current for detecting presence of the particle. Thanks to the use of exponential boosting in modulation of drain-source current in dependence of the gate voltage, the particle 140 may be detected with a high sensitivity.

The effective difference in gate voltage of the FET 110 is a difference between a minimum effective gate voltage and a maximum effective gate voltage. The minimum effective gate voltage and the maximum effective gate voltage may be defined by the particle 140 being arranged in different locations along the extension of the pore 120 from the first side 122 to the second side 124. This may occur e.g. when the pore 120 has a uniform cross-section along the length of the pore 120. However, the pore 120 may alternatively have a non-uniform cross-section, e.g. having tilted walls along the extension of the pore 120, such that the particle 140 only provides blockage of the pore 120 so as to affect the electrical potential distribution in the pore 120 in a single location along the extension of the pore 120. This implies that either the minimum effective gate voltage or the maximum effective gate voltage may be defined when no particle 140 is arranged in the pore 120, such that the effective difference in gate voltage of the FET 110 may be defined in relation to presence and absence of the particle 140 in the pore 120.

A signal level of the drain-source current of the pore FET 110 may be considered to be at a neutral level when no particle is present in the pore 120. When the minimum effective gate voltage and the maximum effective gate voltage are defined by the particle 140 being arranged in different locations, the pore FET sensor 100 may provide a decrease of the signal level compared to the neutral level followed by an increase of the signal level in relation to the neutral level. This may facilitate accurate detection of presence of the particle 140 in the pore 120.

The effective gate voltage is not directly defined by the first voltage $V_{cis}$ or the second voltage $V_{trans}$, respectively. Rather, the effective gate voltage depends on the connection between the first and second electrodes 126, 128, to the gate 118 within the pore 120. Thus, it should be realized that a desired effective difference in gate voltage may not be directly achieved by setting a corresponding difference between the first voltage $V_{cis}$ and the second voltage $V_{trans}$.

Further, it is realized that the drain-source current is proportional to $e^{V_g/V_t}$, where $V_g$ is the effective gate voltage and $V_t$ is a thermal voltage that equals kT/q, where k is Boltzmann's constant, T is temperature of the FET 110, and q is the electron charge. Thus, a difference $\Delta V_g$ between the maximum effective gate voltage and the minimum effective gate voltage $\Delta V_g$ during movement of the particle 140 through the pore 120 will correspond to a difference $e^{\Delta V_g/V_t}$ in drain-source current. This implies that, if the effective difference in gate voltage $\Delta V_g$ is at least kT/q, i.e. approximately 26 mV at room temperature (T=300 K), the exponent factor $\Delta V_g/V_t$ will be larger than 1 so as to provide exponential boosting of the drain-source current in dependence of the effective difference in gate voltage.

When the particle 140 is located within the pore 120, the particle 140 may modify the electrical potential distribution in the pore 120. This implies that the particle 140 may function as a resistive divider defining locations within the fluid wherein voltage drop between the first voltage and the second voltage occur. The location of the particle 140 may thus determine resistive divider values and the effective gate voltage.

When no particle is present in the pore 120, the effective gate voltage will be controlled by an average of the first $V_{cis}$ and the second voltage $V_{trans}$.

Figure 3:
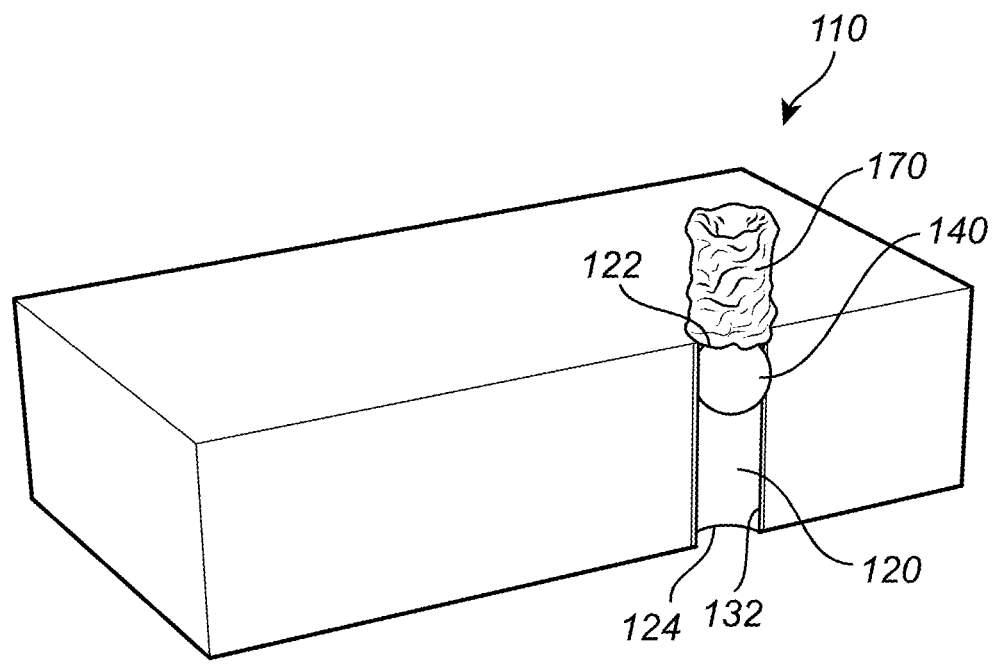
FIGS. 3-4 are schematic views illustrating different locations of a particle moving through the pore.
Figure 4:
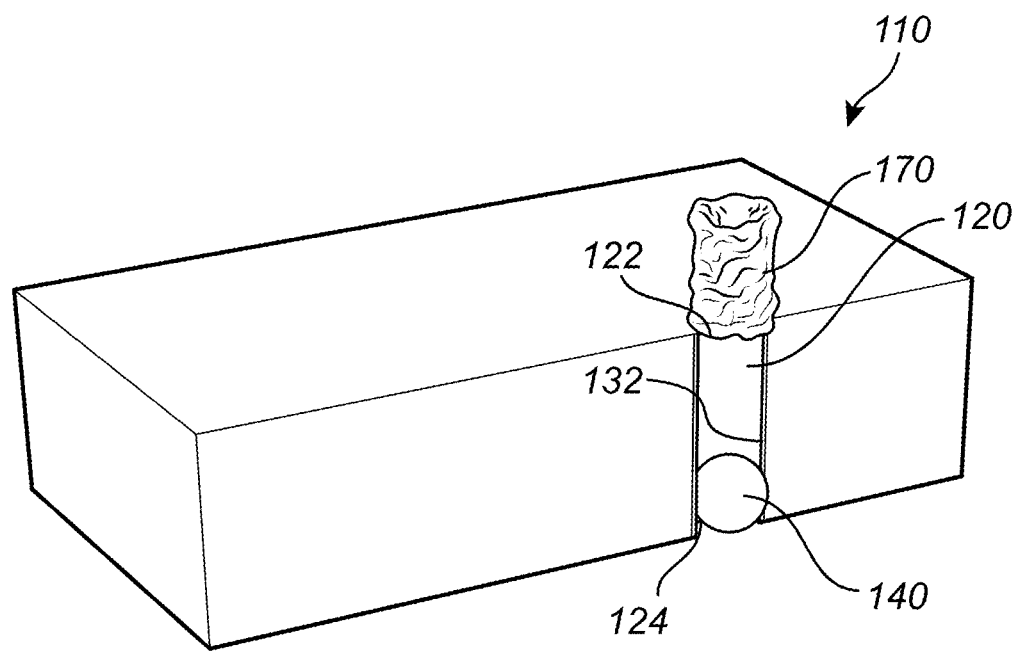

In FIGS. 3-4, the particle 140 is illustrated in relation to a pore 120 having a uniform cross-section along the extension of the pore 120. Thus, the location of the particle 140 functions as a controller to set resistive values in the fluid inside the pore 120. The location of the particle determines resistive divider values and the effective gate voltage. In FIGS. 3-4, the particle 140 is illustrated in two different locations within the pore 120.

In FIG. 3, the particle 140 is illustrated as being arranged at the first side 122 of the pore 120 such that the particle 140 has just entered the pore 120 from the first spacing. In this location, the electrical potential within the pore 120 will be controlled by the second voltage $V_{trans}$ as the particle 140 provides a blockage between the first voltage $V_{cis}$ and the fluid in the pore 120. Thus, the second voltage $V_{trans}$ may define a minimum effective gate voltage of the pore FET 110 in this location.

In FIG. 4, the particle 140 is illustrated as being arranged at the second side 122 of the pore 120 such that the particle 140 is just about to exit the pore 120 into the second spacing. In this location, the electrical potential within the pore 120 will be controlled by the first voltage $V_{cis}$ as the particle 140 provides a blockage between the second voltage $V_{trans}$ and the fluid in the pore 120. Thus, the first voltage $V_{cis}$ may define a maximum effective gate voltage of the pore FET 110 in this location.

It should be realized that the particle 140 need not necessarily move from the location illustrated in FIG. 3 to the location illustrated in FIG. 4. Rather, the particle 140 may move in the opposite direction through the pore 120.

The effective difference in gate voltage in dependence of values of the first voltage $V_{cis}$ and the second voltage $V_{trans}$ may be checked to ensure that the first voltage $V_{cis}$ and the second voltage $V_{trans}$ are set such that the effective difference in gate voltage is at least kT/q. Thus, a minimum difference of $V_{cis/trans}$ may be determined to ensure that exponential boosting is achieved.

A process for determining the minimum difference of $V_{cis/trans}$ may be performed as follows. However, it should be realized that the minimum difference of $V_{cis/trans}$ need not necessarily be determined before the pore FET sensor 100 is operated for detecting particles. Rather, values to be used for the first voltage $V_{cis}$ and the second voltage $V_{trans}$ may be simply selected such that translocation of particles 140 through the pore 120 is detected with a high sensitivity (and thus, the pore FET sensor 100 is operated to provide exponential boosting).

A process for determining the minimum difference of $V_{cis/trans}$ to ensure that the effective difference in gate voltage is at least kT/q may be initiated by setting a common value of the first voltage $V_{cis}$ and the second voltage $V_{trans}$. Then, characteristics of drain-source current as function of the first voltage $V_{cis}$ is determined for the pore FET 110.

Based on the determined characteristics, a value $V_{cis}@I_{off}$ of the first voltage is determined corresponding to the value of the first voltage for a lowest measurable current $I_{off}$ through the pore FET 110 (i.e. when the current reaches noise floor). Further, a value $V_{cis}@I_{on,sat/lin}$ of the first voltage is determined corresponding to the value of the first voltage when the current $I_{on,sat/lin}$ through the pore FET 110 transitions from a linear region to a saturation region.

Then, at least one operating point may be selected, wherein the operating point corresponds to a value of the first voltage $V_{cis}$ between $V_{cis}@I_{and}V_{cis}@I_{on,sat/lin}$. At the at least one operating point, a sensitivity for a very small $V_{cis/trans}$ may be determined. Such sensitivity is considered to correspond to an effect of a local charge of the particle 140 being arranged in the pore 120 on the effective gate voltage. The difference $V_{cis/trans}$ may be selected to be a minimal or almost minimal voltage to allow current flow through the FET 110. For instance, $V_{cis/trans}$ may be set to 10 mV or less than or equal to 5 mV. The small difference $V_{cis/trans}$ to be used may be set by decreasing $V_{trans}$ with respect to $V_{cis}$. Then, the sensitivity may be determined for the small difference $V_{cis/trans}$ by determining a difference in drain-source current between a maximum detected drain-source current and a minimum detected drain-source current comparted to the minimum detected drain-source current. This sensitivity $S_{local\ charge}$ is considered to represent an impact of the local charge of the particle 140 on the effective gate voltage.

Then, impact of resistive divider effect of the particle 140 on the sensitivity is increased by increasing $V_{cis/trans}$ for the at least one selected operating point and the sensitivity of the pore FET sensor 100 is determined. When the sensitivity S reaches $$S = (S_{local\ charge} + 1) * e^1 - 1 = 2.72 * S_{local\ charge} + 1.72$$

the exponent factor equals 1 and the effective difference in gate voltage $\Delta V_g$ is at least kT/q. Hence, for at least such difference $V_{cis/trans}$, exponential boosting is achieved.

As indicated above, the sensitivity of the pore FET sensor 100 may be defined as a difference between the maximum detected drain-source current $I_{max}$ and the minimum detected drain-source current $I_{min}$ compared to the minimum detected drain-source current $I_{min}$, i.e. $(I_{max} - I_{min})/I_{min}$. This sensitivity may be defined between the detected drain-source current when the particle 140 is arranged in two different locations in the pore 120 or may be defined between a current detected when the particle 140 is present in the pore 120 compared to a current detected when no particle 140 is present in the pore 120.

According to an embodiment, the first voltage $V_{cis}$ and the second voltage $V_{trans}$ are controlled to set the effective difference in gate voltage such that the sensitivity is larger than 100%, or more preferably such that the sensitivity is larger than 200%. At such sensitivities, particles 140 passing through the pore 120 may be accurately detected.

Operation of the pore FET sensor 100 may involve determining a maximum sensitivity that could be achieved. However, it should be realized that the pore FET sensor 100 may well be operated with a lower sensitivity while still enabling accurate detection of particles 140. Thus, determination of the maximum sensitivity need not be performed. However, in case maximum sensitivity is of importance, the operation of the pore FET sensor 100 may involve calibrating the pore FET sensor 100 for setting the maximum sensitivity.

The calibrating comprises setting the first voltage $V_{cis}$ equal to the second voltage $V_{trans}$. Then, characteristics of drain-source current as function of the first voltage is determined for the pore FET sensor 100.

Based on the determined characteristics, an off voltage value $V_{cis}@I_{off}$ of the first voltage is determined corresponding to the value of the first voltage for a lowest measurable current $I_{off}$ through the pore FET 110 (i.e. when the current reaches noise floor). Further, a saturation voltage value $V_{cis}@I_{on,sat/lin}$ of the first voltage is determined corresponding to the value of the first voltage when the current $I_{on,sat/lin}$ through the pore FET 110 transitions from a linear region to a saturation region.

Then, the first electrode 126 is biased to set the first voltage $V_{cis}$ to the saturation voltage value $V_{cis}@I_{on,sat/lin}$ and the second electrode 128 is biased to set the second voltage $V_{trans}$ to the off voltage value $V_{cis}@I_{off}$.

Then, an iteration of increasing the first voltage $V_{cis}$ and decreasing the second voltage $V_{trans}$ is performed until the effective gate voltage when a particle 140 is arranged in the pore 120 at the first side 122 corresponds to the off voltage value $V_{cis}@I_{off}$ and the gate voltage when the particle 140 is arranged in the pore 120 at the second side 124 corresponds to the saturation voltage value $V_{cis}@I_{on,sat/lin}$.

Based on such calibration, values of the first voltage $V_{cis}$ and the second voltage $V_{trans}$ to be used in operation of the pore FET sensor 100 may be determined to correspond to the end values of the iterative increasing of the first voltage $V_{cis}$ and decreasing of second voltage $V_{trans}$.

It should be realized that the calibration described above is made in relation to a pore FET sensor 100 for which the maximum effective gate voltage and the minimum effective gate voltage are provided by two different locations of the particle 140 in the pore 120. However, maximum sensitivity may be determined in a similar manner as well for pore FET sensor 100 wherein either the minimum effective gate voltage or the maximum effective gate voltage may be defined when no particle 140 is arranged in the pore 120, such that the effective difference in gate voltage of the FET 110 may be defined in relation to presence and absence of the particle 140 in the pore 120.

The voltage difference $V_{cis/trans}$ between the first voltage $V_{cis}$ and the second voltage $V_{trans}$ may have a double functionality in ensuring that the effective difference in gate voltage of the FET 110 provides exponential boosting of the drain-source current in dependence of the effective difference in gate voltage and in additionally driving the particle 140 through the pore 120.

The voltage difference $V_{cis/trans}$ provides a force acting on charged particles 140 for driving the charged particles 140 through the fluid and through the pore 120. If the particles 140 are positively charged, the particles 140 are driven from the first side 122 to the second side 124 of the pore 120 towards the lower potential set by the second voltage $V_{trans}$.

If the particles 140 are negatively charged, the particles 140 are instead driven from the second side 124 to the first side 122.

However, the pore FET sensor 100 may alternatively or additionally drive particles 140 through the pore 120 based on other means. For instance, the pore FET sensor 100 may be provided with a controller for controlling a pressure of the first spacing and the second spacing. The controller may thus set a pressure difference between the first spacing and the second spacing so as to provide a pressure difference between the first side 122 and the second side 124 of the pore 120, which may drive particles 140 through the pore 120. This may be particularly useful for driving uncharged particles 140 through the pore 120.

According to another alternative, the pore FET sensor 100 may make use of electro-osmosis for driving particles 140 through the pore 120. The pore FET sensor 100 may comprise a controller for controlling a concentration of particles 140 and/or of ions in the electrolyte fluid between the first spacing and the second spacing. Thus, based on the concentration difference there may be a net flow of the electrolyte fluid through the pore 120 and the net flow may drag particles 140 along the flow in the fluid. This may also be particularly useful for driving uncharged particles 140 through the pore 120.

According to embodiments, as illustrated in FIGS. 3-4, a biological membrane may be arranged at the first side 122 of the pore 120 having a biological pore 170 aligned with the pore 120 for assisting in driving particles to be detected through the pore 120. The biological membrane may control a speed of the particle 140 through the biological membrane.

In particular, in combination with an enzyme, a speed of DNA passing through the biological pore 170 may be reduced compared to if DNA passes through the biological pore 170 without the enzyme. Hence, the biological membrane may slow down speed of particles 140, which also implies that the speed of particles 140 through the pore 120 may be slowed down. A lower speed of the particle 140 through the pore 120 allows use of a lower sampling rate of the drain-source current in the pore FET sensor 100, which may be used for improving a signal-to-noise ratio for detecting the particle 140.

According to an embodiment, the detecting of the presence of the particle 140 in the pore 120 may involve read-out of the detected drain-source current to a processing unit. The detected drain-source current may or may not be subject to analog-to-digital conversion before further processing of the detected drain-source current. If the detected drain-source current is converted to digital form, processing in a physical unit external to the pore FET sensor 100 is facilitated and the read-out of the detected drain-source current may thus be transmitted to an external processing unit. Also, a sequence of read-out values of the detected drain-source current may be stored and/or transmitted to the processing unit such that processing of the detected drain-source current need not be performed simultaneously with acquiring of the detected drain-source current.

The detected drain-source current may thus be analyzed through processing so as to identify change(s) in the drain-source current, which may be interpreted as corresponding to particle(s) 140 to be detected being passed through the pore 120. Different types of particles 140 may be identified based on different levels of change in the drain-source current.

It should be realized that the drain-source current will increase for increasing effective gate voltage if the pore FET 110 is an n-channel FET. In contrast, the drain-source current will decrease for increasing effective gate voltage if the pore FET 110 is a p-channel FET.

It should further be realized that although a single pore FET sensor 100 is shown and discussed above, a system may comprise a plurality of pore FET sensors 100, which may for instance be arranged in an array so as to allow detecting particles 140 in parallel in a plurality of samples or in a plurality of positions of a sample.

A size of the pore 120 should be dimensioned to fit a size of the particle 140 to be detected. It should be realized that the pore FET sensor 100 may be designed during manufacture with an intent for the pore FET sensor 100 to be used with a particular type of particle 140 such that the pore FET sensor 100 will be adapted for such use. For instance, if DNA is to be analyzed, the size of the particle 140 to be detected is well-defined and the pore FET sensor 100 can be manufactured to be adapted for use in detection of DNA.

The particle 140 may be used for providing a resistive divider effect in the pore 120. This implies that the particle 140 should have a size corresponding to a substantive portion of the cross-section of the pore 120 such that the particle 140 will form a blockage in the pore and modify the electrical potential distribution in the pore 120. In particular, the particle 140 should modify the electrical potential distribution in the pore 120 at a smallest cross-section of the pore 120. Where the pore 120 has a uniform cross-section, the particle 140 will affect the electrical potential distribution in the pore 120 in each location of the particle 140 along the extent of the pore 120.

Also, it should be realized that the particle 140 may have a maximum cross-section that may define a cross-sectional size of the particle 140.

According to an embodiment, the particle 140 to be detected is uncharged, and an area of the maximum cross-section of the particle 140 is larger than 50% of the area of the minimum cross-section of the pore 120.

According to another embodiment, the particle 140 to be detected is charged, and the area of the maximum cross-section of the particle 140 is larger than 10% of the area of the minimum cross-section of the pore 120.

A surface of the pore 120 along the extension from the first side 122 to the second side 124 may be provided with surface charges. The surface charges may have an opposite sign to the charge of the particle 140 to be detected. Preferably, a concentration of the surface charges is in a range of $1\text{-}10 \ast 10^{13}$ cm$^{-2}$.

Having surface charges on the surface of the pore 120 implies that the fluid in the pore 120 may exhibit charge carriers of an opposite sign to the surface charges. Hence, when the particle 140, having an opposite sign to the surface charges, is moved through the pore 120, there may be a local depletion of charges of the same sign as the particle 140 in the fluid. The local depletion is induced by the particle 140 being arranged in the pore 120. This implies that the introduction of the particle 140 in the pore 120 may change the fluid current flow through the pore 120 to a large extent so as to increase effective difference in the gate voltage when the particle 140 is moved through the pore 120.

According to an alternative, the surface charges have a same sign as the charge of the particle 140 to be detected.

When the particle 140, having a same sign as the surface charges, is moved through the pore 120, there may be a local increase of charges of the opposite sign to the particle 140 in the fluid. Thus, around the particle 140 being arranged in the pore 120, resistance drops giving rise to a change in electrostatic potential in the pore 120, which may be detected as an effective difference in the gate voltage when the particle 140 is moved through the pore 120.

Surface charges may be formed on the surface of the pore 120 by ionization of molecules at the surface of the thin dielectric layer 132. This may be caused by exposing the pore FET 110 to the electrolyte fluid. For instance, if silicon dioxide (SiO$_2$) is used as the thin dielectric layer 132, silanol groups form when the silicon dioxide is immersed in an aqueous solution (which may be used as the electrolyte fluid), and ionization of silanol molecules at the surface of the thin dielectric layer 132 would form negative surface charges on the surface of the pore 132 for a neutral (pH=7) solution. Charge density may have a dependence of pH value of the electrolyte fluid, such that control of pH value may provide a control of concentration and sign of the surface charges.

It would also be possible to form positive surface charges on the surface of the pore 132 and/or to control the concentration of surface charges.

Figure 5:
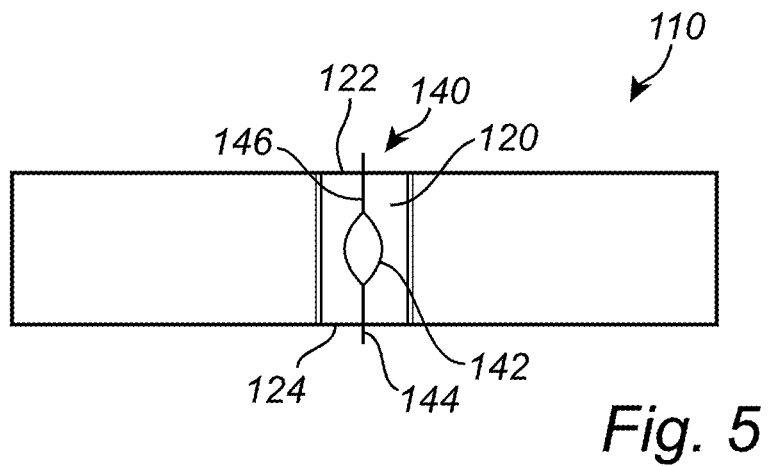
FIG. 5 is a schematic view illustrating an elongate particle in the pore.

Referring now to FIG. 5, a length of the pore 120 is illustrated in relation to a length of the particle 140. The length of the pore 120 along the extension from the first side 122 to the second side 124 should be longer than the particle 140.

However, as illustrated in FIG. 5, the particle 140 may have a relatively large cross-section in a portion 142 of the particle 140, whereas the particle 140 may have relatively narrow portions 144, 146 on at least one side of the portion 142 having a large cross-section. The narrow portions 144, 146 would not affect the electrical potential distribution in the pore 120 and, hence, not affect the effective gate voltage of the pore FET 110. This implies that it may be only the portion 142 having a large cross-section that affects the effective gate voltage, such that the pore 120 should have a length that is larger than the length of the portion 142.

The narrow portions 144, 146 may have a cross-section that is substantially smaller than 50% of a minimum area of the pore 120, if the narrow portions 144, 146 are uncharged, such as having a cross-section that is smaller than 10% of a minimum area of the pore 120 or smaller than 5% of a minimum area of the pore 120.

The narrow portions 144, 146 may have a cross-section that is substantially smaller than 10% of a minimum area of the pore 120, if the narrow portions 144, 146 are charged, such as having a cross-section that is smaller than 2% of a minimum area of the pore 120 or smaller than 1% of a minimum area of the pore 120.

In some embodiments, charges of the particle 140 may be distributed in the portion 142 having a large cross-section, whereas no charges are provided in narrow portions 144, 146. This further emphasizes that the portion 142 is relevant for affecting the gate voltage, whereas the narrow portions 144, 146 do not affect the gate voltage.

Thanks to the pore 120 being longer than the particle 140 or at least being longer than the portion 142 of the particle 140 that effectively affects the electrical potential distribution in the pore 120, the portion 142 of the particle 140 cannot be arranged simultaneously at the first side 122 and at the second side 124 of the pore 120 such that a substantial effective difference in gate voltage during movement of the particle 140 in the fluid may be detected. This implies that the signal level of the drain-source current of the pore FET 110 as a particle 140 is moved through the pore 120 will go from a neutral level, to a low level, lower than the neutral level, followed by a high level, higher than the neutral level, and then going back to the neutral level as the particle 140 leaves the pore 120. This ensures accurate detection of the particle 140 by the pore FET sensor 100.

However, it should be realized that the pore 120 may be shorter than the particle 140 while still allowing the particle 140 to be correctly detected. Then, as a particle 140 is moved through the pore 120, the signal level of the drain-source current may go from a neutral level, to a small level (when the particle 140 is entering the pore 120 at the first side 122), to a neutral level (when the particle 140 is extending from the first side 122 to the second side 124), to a high level (when the particle 140 is leaving the pore 120 at the second side 124) and back to the neutral level. The particle 140 may also be detected by such modulation of the drain-source current.

The pore FET sensor 100 may be provided with a controller for ensuring that the particles 140 in the fluid are introduced one at a time in the pore 120. This may imply that particles 140 will be sequentially introduced into the pore 120 such that a previous particle has left the pore 120 before a next particle enters the pore 120. This may be ensured e.g. using a biological membrane for assisting particles 140 to be introduced into the pore 120.

Thanks to sequential particles 140 not being simultaneously in the pore 120, a substantial effective difference in gate voltage during movement of a single particle 140 through the pore 120 may be detected. This ensures accurate detection of the particle 140 by the pore FET sensor 100.

Figure 6:
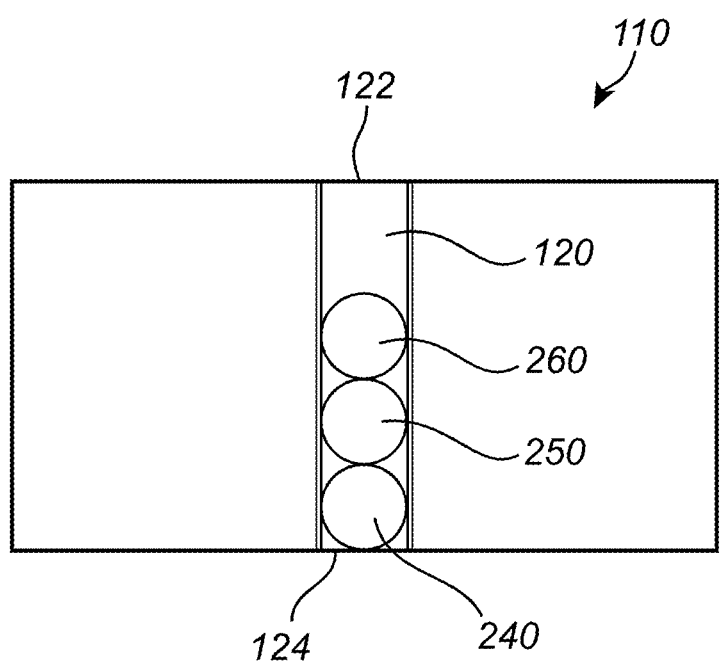
FIG. 6 is a schematic view illustrating multiple particles in the pore.

However, referring now to FIG. 6, multiple particles 240, 250, 260 may be introduced in a sequence into the pore 120 forming a chain through the pore 120. The multiple particles 240, 250, 260 may be controlled to be introduced into the pore 120 such that the length of the chain is shorter than 70% of the length of the pore 120. According to another embodiment, the multiple particles 240, 250, 260 may be controlled to be introduced into the pore 120 such that the length of the chain is shorter than 50% of the length of the pore 120.

Thanks to the pore being longer than the chain of multiple particles 240, 250, 260, there will not be particles arranged simultaneously at the first side 122 and at the second side 124 of the pore 120 such that a substantial effective difference in gate voltage during movement of the multiple particles 240, 250, 260 in the fluid may be detected. This ensures accurate detection of the multiple particles 240, 250, 260.

Figure 7:
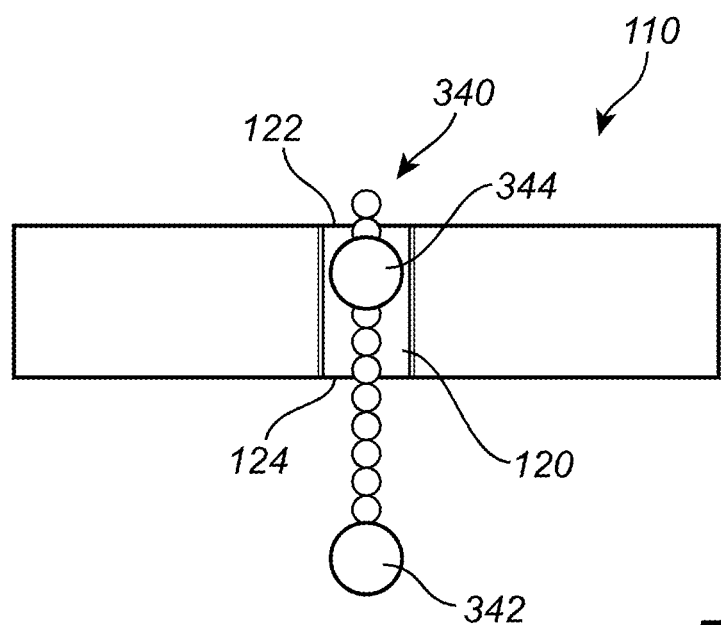
FIG. 7 is a schematic view illustrating a single particle extending through the pore, wherein the particle is provided with labels for detecting sites of the particle.

Referring now to FIG. 7, a single particle 340 may be longer than the pore 120. For instance, the single particle 340 may have a form of a long chain. The single particle 340 may be provided with multiple labels 342, 344. The labels 342, 344 may be configured to allow detection of the labels 342, 344 when the single particle 340 is moved with the labels 342, 344 through the pore 120. Thus, the particle 340 may have a relatively small cross-section, such that, without being provided with labels 342, 344, the particle 340 does not substantially affect the electrical potential distribution in the pore 120. The labels 342, 344 may have a large cross-section and may be charged such that the labels 342, 344 are adapted to highly affect the electrical potential distribution in the pore 120 so as to enable accurate detection of the labels 342, 344.

The labels 342, 344 may be selectively bonded to sites of the chain of the particle 340. Thus, by providing sites with labels 342, 344, the particle 340 may be analyzed through detection of the labels 342, 344.

The particle 340 has a distance between sites to which labels 342, 344 will be bonded which defines a distance between adjacent labels 342, 344 being bonded to the particle 340. The pore 120 may be dimensioned in relation to the particle 340 such that the length of the pore 120 is shorter than 70% of a distance between adjacent labels 342, 344 among the multiple labels. Advantageously, the length of the pore 120 is shorter than 50% of a distance between adjacent labels 342, 344 among the multiple labels.

Thanks to the pore being shorter than 70%, or shorter than 50%, of a distance between adjacent labels 342, 344, there will not be labels arranged simultaneously at the first side 122 and at the second side 124 of the pore 120 such that a substantial effective difference in gate voltage during movement of the particle 340 through the pore 120 may be detected. This ensures accurate detection of the multiple labels 342, 344 bonded to a common long chain of the particle 340.

Since the labels 342, 344 are detected and separated between sites of the particle 340, the chain of the particle 340 may have any length without affecting the detection by the pore FET sensor 100.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method of operating a pore field-effect transistor sensor for detecting particles, wherein the pore field-effect transistor sensor comprises a field-effect transistor having a source, a drain, a dielectric gate, and a channel region between the source and the drain, wherein the gate is controlled by a pore filled by an electrically conducting fluid and the pore is configured to extend from a first side to a second side to provide gating of the field-effect transistor from within the pore, and wherein the pore field-effect transistor sensor further comprises a first electrode for setting a first voltage at the first side of the pore and a second electrode for setting a second voltage at the second side of the pore, wherein said method comprises:
    controlling the first voltage to set the field-effect transistor in a subthreshold region;
    controlling the second voltage to set a voltage difference between the first voltage and the second voltage such that an effective difference in gate voltage of the field-effect transistor experienced between a minimum effective gate voltage and a maximum effective gate voltage during movement of a particle to be detected in the fluid, wherein the movement of the particle to be detected includes the particle to be detected being outside the pore and being passed through the pore, is at least kT/q, where k is Boltzmann's constant, T is temperature of the field-effect transistor, and q is the electron charge;
    detecting a drain-source current in the field-effect transistor, wherein the particle to be detected passing through the fluid in the pore is configured to modulate the drain-source current for detecting presence of the particle; and
    calibrating the pore field-effect transistor sensor for setting a maximum sensitivity, wherein the calibrating comprises:
        setting the first voltage equal to the second voltage to obtain characteristics of drain-source current in relation to the first voltage;
        determining an off voltage value of the first voltage corresponding to a lowest measurable current of the drain-source current;

determining a saturation voltage value of the first voltage corresponding to a transition from linear to saturation region of the field-effect transistor;

biasing the first voltage using the saturation voltage value and biasing the second voltage using the off voltage value;

iteratively increasing the first voltage and decreasing the second voltage until the gate voltage when a particle is arranged in the pore at the first side corresponds to the off voltage value and the gate voltage when the particle is arranged in the pore at the second side corresponds to the saturation voltage value; and determining first voltage value and second voltage value to be used in operation of the pore field-effect transistor sensor based on end values of the iterative increasing of the first voltage and decreasing of second voltage.

2. The method according to claim 1, wherein the pore is configured to extend through the channel region between the source and the drain.

3. The method according to claim 1, wherein the first and second voltages are controlled to set the effective difference in gate voltage such that a difference between a maximum detected drain-source current compared to a minimum detected drain-source current is larger than 100% of the minimum detected drain-source current.

4. The method according to claim 1, wherein the particle to be detected has a size in relation to the pore so as to modify electrical potential distribution in the pore such that location of the particle to be detected functions as a controller to set resistive values in the fluid inside the pore such that the location of the particle determines resistive divider values and the effective gate voltage.

5. The method according to claim 1, wherein an area of a minimum cross-section of the pore is set in relation to the particle to be detected such that an area of a maximum cross-section of the particle to be detected is larger than 50% of the area of the minimum cross-section of the pore, if the particle to be detected is uncharged, and the area of the maximum cross-section of the particle to be detected is larger than 10% of the area of the minimum cross-section of the pore, if the particle to be detected is charged.

6. The method according to claim 1, wherein the pore has a uniform cross-section along the extension from the first side to the second side.

7. The method according to claim 1, wherein a length of the pore along the extension from the first side to the second side is longer than a length of the particle to be detected affecting the gate voltage.

8. The method according to claim 1, further comprising providing surface charges on a surface of the pore along the extension from the first side to the second side, wherein the surface charges are of an opposite sign to a charge of the particle to be detected.

9. The method according to claim 1, further comprising identifying multiple particles to be detected passing through the fluid in the pore forming a chain through the pore, wherein the length of the chain is shorter than 70% of a length of the pore along the extension from the first side to the second side.

10. The method according to claim 1, wherein the particle to be detected comprises multiple labels bonded to sites of a long chain, wherein a length of the pore along the extension from the first side to the second side is shorter than 70% of a distance between adjacent labels among the multiple labels.

11. The method according to claim 1, wherein the pore is a solid-state pore formed in a solid-state material.

12. The method according to claim 1, wherein a biological membrane is arranged at the first side of the pore and having a biological pore aligned with the pore for assisting in driving particles to be detected through the pore.

13. The method according to claim 2, wherein the dielectric of the pore is provided with a first dielectric layer at the surface of the pore along the extension from the first side to the second side, and wherein a surface of the channel region facing an electrolyte fluid at the first side and the second side, respectively, is provided with a second dielectric layer, wherein the second dielectric layer is thicker than the first dielectric layer.

14. The method according to claim 1, wherein the pore is a nanopore having a cross-sectional diameter smaller than 10 nm.

* * * * *